US012642977B2

(12) United States Patent
von Arx et al.

(10) Patent No.: US 12,642,977 B2
(45) Date of Patent: Jun. 2, 2026

(54) IMPLANTABLE MEDICAL DEVICE COMPRISING AN ELECTRICAL LINE FORMING AN ANTENNA

(71) Applicant: BIOTRONIK SE & Co. KG, Berlin (DE)

(72) Inventors: Jeffrey A. von Arx, Lake Oswego, OR (US); Yu Wang, Lake Oswego, OR (US); James E. Brown, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 255 days.

(21) Appl. No.: 18/558,767

(22) PCT Filed: May 25, 2022

(86) PCT No.: PCT/EP2022/064340
§ 371 (c)(1),
(2) Date: Nov. 3, 2023

(87) PCT Pub. No.: WO2022/253691
PCT Pub. Date: Dec. 8, 2022

(65) Prior Publication Data
US 2024/0238598 A1     Jul. 18, 2024

Related U.S. Application Data

(60) Provisional application No. 63/195,402, filed on Jun. 1, 2021.

(30) Foreign Application Priority Data

Jul. 1, 2021     (EP) ..................................... 21183024

(51) Int. Cl.
*A61N 1/37*          (2006.01)
*A61N 1/02*          (2006.01)
(Continued)

(52) U.S. Cl.
CPC ......... *A61N 1/37229* (2013.01); *A61N 1/025* (2013.01); *A61N 1/05* (2013.01);
(Continued)

(58) Field of Classification Search
CPC .......... A61N 1/025; A61N 1/05; A61N 1/362; A61N 1/37217; A61N 1/37229; A61N 1/3754; A61N 1/3758; A61N 1/39
See application file for complete search history.

(56) References Cited

U.S. PATENT DOCUMENTS

2003/0032997 A1*   2/2003   Pianca ................. A61N 1/0534
                                                                     607/117
2005/0055068 A1*   3/2005   Von Arx ............ A61N 1/37229
                                                                     607/32

(Continued)

OTHER PUBLICATIONS

International Search Report (PCT/ISA/210) and Written Opinion (PCT/ISA/237) mailed on Jul. 11, 2022, by the European Patent Office as the International Searching Authority for International Application No. PCT/EP2022/064340. (9 pages).

*Primary Examiner* — Amanda K Hulbert
(74) *Attorney, Agent, or Firm* — Buchanan Ingersoll & Rooney PC

(57)                    ABSTRACT
An implantable medical device comprises an electronics module comprising communication circuitry for at least one of transmitting communication signals to and receiving communication signals from an external communication device, and further comprising processing circuitry for at least one of processing sensed biological signals and generating stimulation signals for emission. An electrode arrangement serves for at least one of sensing said biological signals of a patient and emitting said stimulation signals. An electrical line extends in between the electronics module and the electrode arrangement, wherein the electrical line comprises a first line section, a second line section and a
(Continued)

decoupling element, the first line section being electrically decoupled at RF frequencies from the second line section by the decoupling element and forming an antenna for at least one of transmitting and receiving said communication signals.

15 Claims, 2 Drawing Sheets

(51) Int. Cl.

| | | |
|---|---|---|
| *A61N 1/05* | (2006.01) | |
| *A61N 1/362* | (2006.01) | |
| *A61N 1/372* | (2006.01) | |
| *A61N 1/375* | (2006.01) | |
| *A61N 1/39* | (2006.01) | |

(52) U.S. Cl.
CPC ........... *A61N 1/362* (2013.01); *A61N 1/3754* (2013.01); *A61N 1/3758* (2013.01); *A61N 1/39* (2013.01)

(56) References Cited

U.S. PATENT DOCUMENTS

| | | |
|---|---|---|
| 2016/0250483 A1 | 9/2016 | Klimovitch et al. |
| 2017/0065207 A1 | 3/2017 | Landherr et al. |
| 2018/0020919 A1 | 1/2018 | Hess |

\* cited by examiner

IMPLANTABLE MEDICAL DEVICE COMPRISING AN ELECTRICAL LINE FORMING AN ANTENNA

CROSS-REFERENCE TO RELATED APPLICATIONS

This application is the United States National Phase under 35 U.S.C. § 371 of PCT International Patent Application No. PCT/EP2022/064340, filed on May 25, 2022, which claims the benefit of European Patent Application No. 21183024.5, filed on Jul. 1, 2021, and U.S. Provisional Patent Application No. 63/195,402, filed on Jun. 1, 2021, the disclosures of which are hereby incorporated by reference herein in their entireties.

TECHNICAL FIELD

The instant invention generally relates to an implantable medical device which is to be implanted into a patient for serving a diagnostic and/or therapeutic function.

BACKGROUND

An implantable medical device of this kind may, for example, be a pacemaker, an implantable cardioverter defibrillator, a sensor device such as an implantable bio-sensor for measuring a blood pressure or another biological signal, or a recording device such as an implantable loop recorder to be subcutaneously implanted in a patient.

An implantable pacemaker may, for example, be subcutaneously implanted in a patient and may comprise, e.g., leads carrying electrodes and extending from a generator unit of the pacemaker device into the patient's heart, for example, to provide a pacing action in the right ventricle of the heart.

An implantable cardioverter defibrillator may serve for monitoring and treating potentially life-threatening arrhythmias in a patient's heart, wherein a cardioverter defibrillator of this kind may, for example, be implanted subcutaneously and may comprise leads extending into the patient's heart in order to record signals and to inject stimulation energy into the patient's heart, for example, to provide an electric shock (defibrillation).

Implantable sensor devices, such as pressure sensors, flow sensors, temperature sensors or the like, may, for example, be implanted subcutaneously or into a blood vessel, such as a vein, in order to provide for a monitoring of relevant parameters, e.g., cardiac signals, in the context of providing a therapy or of home-monitoring.

An implantable loop recorder (ILR) is, for example, subcutaneously implanted and serves to continuously record information, for example, about cardiac activity, such as an ECG. An ILR may continuously loop its memory and may store particular portions of signals, such that recorded signals may be communicated to an external device for analyzing the signals and for providing a diagnosis.

An implantable medical device of the kind concerned herein generally comprises an electronic module comprising communication circuitry for at least one of transmitting communication signals to and receiving communication signals from an external communication device, and further comprising processing circuitry for at least one of processing sensed biological signals and generating stimulation signals for emission. An electrode arrangement serves for at least one of sensing biological signals of a patient and emitting stimulation signals. Communication with an exter-nal communication device is established using an antenna for transmitting and/or receiving communication signals.

As the RF antenna must be located external to the device housing, and it is desirable to have a smaller device volume, the antenna is often co-located in the device header with other elements of the device. Generally, in an implantable medical device of this kind, the antenna should be arranged at a physical distance with respect to the other electrically conductive components of the device, such that operation of the antenna is disturbed minimally. For example, in a bio-sensor device the antenna may be placed on a so-called header portion extending from a main housing portion. As the header portion may carry multiple functional components, such as parts of the electrode arrangement, there is a desire to provide a device of simple structural built with a manageable complexity for interconnecting components of the header with the electronics module within the main housing portion of the implantable medical device.

U.S. Publication No. 2016/0250483 A1 discloses an implantable medical device which is configured to be implanted within a patient, the implantable medical device including a controller configured to adjust a communication frequency, a housing formed of an electrically common material, and an insulating cover coupled to the housing.

The present disclosure is directed toward overcoming one or more of the above-mentioned problems, though not necessarily limited to embodiments that do.

SUMMARY

It is an object of the instant invention to provide an implantable medical device using an antenna for communication with an external device allowing for an integration of the antenna in a cost-efficient, yet electrically reliable manner.

In one aspect, an implantable medical device comprises an electronics module comprising communication circuitry for at least one of transmitting communication signals to and receiving communication signals from an external communication device, and further comprising processing circuitry for at least one of processing sensed biological signals and generating stimulation signals for emission: an electrode arrangement for at least one of sensing said biological signals of a patient and emitting said stimulation signals: an antenna for at least one of transmitting and receiving said communication signals; and an electrical line extending in between the electronics module and the electrode arrangement, wherein the electrical line comprises a first line section, a second line section and a decoupling element, the first line section being electrically decoupled from the second line section by the decoupling element and forming said antenna.

Accordingly, the implantable medical device comprises an electrode arrangement for sensing or emitting signals in the context of a diagnostic or therapeutic function. In addition, the implantable medical device comprises an antenna for transmitting and/or receiving communication signals for establishing a communication with an external communication device, such as an external monitoring device, which is placed outside of the patient. By means of the antenna, for example information relating to sensed biological signals may be transferred towards the external communication device, or configuration data may be received from the external communication device in order to adapt a configuration of the implantable medical device.

Herein, the electrode arrangement is connected to the electronics module of the implantable medical device using an electrical line, which in addition serves to form the antenna. Hence, a single electrical interconnection is sufficient for connecting the antenna and the electrode arrangement to the electronics module, thus reducing the complexity of interconnections within the implantable medical device. Thus, the antenna is formed by a single wire. By forming the antenna by a line section of the electrical line, no separate components, interconnections or hermetic feedthroughs are required for the antenna, hence obtaining an implantable medical device of simple and cost-efficient structure with respect to the arrangement of the antenna and the electrode arrangement. Thus, the antenna is an integral and not detachable part of the implantable medical device.

The electrical line extends in between the electronics module and the electrode arrangement. Herein, a first line section of the electrical line forms the antenna, wherein the line section of the electrical line associated with the antenna is decoupled from another, second line section of the electrical line by means of a decoupling element. Hence, using the decoupling element only the first line section is electrically active for receiving communication signals and hence serves as the antenna, wherein the further, second line section is functionally separated from the first line section such that it does not influence a transmission or reception of communication signals by means of the first line section.

By means of the antenna in particular communication signals in the shape of RF signals may be transmitted and/or received. Such communication signals may in particular lie in a communication frequency range above 500 MHz, preferably above 1 GHz, for example in a communication frequency range between 2 GHz and 3 GHz.

The communication circuitry in particular may be configured to establish a communication using a standardized communication protocol, such as, for example, a Zigbee protocol or a Bluetooth protocol, for example a Bluetooth Low Energy (BLE) protocol. For example, if a communication is to be established using the Bluetooth Low Energy technology, a communication frequency range may lie between 2.4 GHz and 2.4835 GHZ, relating to the standard Bluetooth Low Energy frequency band.

In order to achieve an effective signal transmission and signal reception in a desired communication frequency range, the electrical length of the first line section forming the antenna should be chosen such that the electrical length of the line section is optimized for that communication frequency range. In particular, the first line section may be formed to have an electrical length substantially equal to a quarter wavelength at a communication frequency, for example at a center frequency of a communication frequency range, for example in between 2.4 GHz and 2.4835 GHZ, e.g., when using the Bluetooth Low Energy technology.

Generally, at open space the quarter wavelength at a communication frequency in between 2.4 GHz and 2.4835 GHz would lie at about 31 mm. However, as the implantable medical device in an implanted state is surrounded by tissue (which is often conductive) and as in addition the electrical line forming the antenna may be encapsulated by a dielectric material, for example a silicone material for electrical insulation, the effective electrical wavelength is shortened when taking the effective dielectric constants of the surrounding material and the conductivity of the body tissue into account, such that the quarter wavelength may, for example, lie in between 3 mm and 5 mm. Hence, the quarter wavelength is to be computed in view of the actual, intended implementation in order to choose an optimal physical length of the antenna.

For example, dependent also on the communication frequency range that shall be used for communication, the first line section forming the antenna may comprise a physical length in between 2 mm and 20 mm, for example between 3 mm and 10 mm, for example at about 4 mm.

In one embodiment, the decoupling element is configured to block signals in said communication frequency range and to pass signals in a physiological frequency range below said communication frequency range. For example, the decoupling element may be configured such that at a communication frequency, for example within the Bluetooth Low Energy frequency range between 2.4 GHz and 2.4835 GHZ, the decoupling element may comprise a rather large impedance, for example larger than 100 Ohm, in particular larger than 200 Ohm, such that the first line section electrically is separated from the second line section and hence only the first line section is electrically active for receiving or transmitting signals within the communication frequency range. However, in a physiological frequency range—that is in a frequency range in which physiological signals occur—the decoupling element effectively is electrically conductive and for this comprises a small impedance, for example below 1 Ohm, preferably below 0.1 Ohm, even more preferably smaller than 0.01 Ohm, such that within the physiological frequency range the electrical line functions as a single conductive line without electrical separation of the line sections. Hence, in the physiological frequency range the electrode arrangement is electrically connected to the electronics module, such that sensed signals may be received via the electrode arrangement, and stimulation signals may be transmitted via the electrode arrangement.

In one embodiment, the decoupling element comprises an inductance. The inductance may, for example, have an inductance value between 5 nH and 50 nH, for example in between 10 nH and 30 nH, for example 20 nH. Note that at 2.4 GHZ, 20 nH equals an impedance of 301$\Omega$, while at 1 KHz (biological signal range), 20 nH equals an impedance of $1.3*10^{-4}\Omega$.

In one embodiment, the electrical line is formed by a continuous wire, the decoupling element being formed by at least one coil winding arranged in between the first line section and the second line section and formed by the continuous wire. In this embodiment, the line sections and the decoupling element are formed by a single, continuous wire, wherein the line sections are decoupled from one another in an electrical sense at a communication frequency by forming one or multiple windings within the wire to provide the decoupling element. For example, the decoupling element may be formed by two, three, four, five, six or more winding turns to provide for an inductance to achieve a decoupling at the communication frequency, but to allow physiological signals to pass.

In another embodiment, the electrical line is formed by discontinuous wire sections, a first wire section forming the first line section and a second wire section forming the second line section. In this embodiment the electrical line is not formed by a continuous wire, but by separate wire sections. In this embodiment, the decoupling element may, for example, be formed by a discrete inductor element which is placed in between the wire sections forming the first line section and the second line section, such that the wire sections are electrically interconnected by means of the discrete inductor.

The electrical line is in one embodiment encapsulated by an electrically insulating housing. For example, the electrical line may be encapsulated by a housing formed from a silicone material or another material which is flexibly deformable. In another embodiment, the housing may be formed from an epoxy, a polyurethane or another rigid material, such that the housing is not flexibly deformable, but comprises a rigid shape.

In one embodiment, the electrical line is formed from an MP35N wire, a gold wire, a platinum wire, a platinum-iridium wire, a Drawn Filled Tubing (DFT) wire of MP35N with a silver core, or a Drawn Filled Tubing (DFT) wire of MP35N with a tantalum core.

In one embodiment, the implantable medical device comprises a housing forming a main housing portion and a header portion extending from the main housing portion. The electronics module may, for example, be arranged in or on the main housing portion, whereas the electrical line is arranged in or on the header portion. The header portion may, for example, extend linearly from the main housing portion, wherein the header portion may be flexibly deformable, or may have a rigid structure such that it is not flexibly deformable.

Herein, the electrode arrangement may be arranged on an end of the header portion which is distal with respect to the main housing portion. The electrical line may, for example, extend along the header portion, such that by means of the electrical line the electrode arrangement is electrically connected to the electronics module arranged in or on the main housing portion.

In another embodiment, the implantable medical device may, for example, be formed by a combination of a generator and at least one lead extending from the generator, such as it is the case, for example, in a pacemaker device or a cardioverter defibrillator which is to be implanted subcutaneously in a patient. In this case the electrode arrangement may be placed on a lead extending from the generator housing, wherein the electrical line may extend along the lead. The at least one lead may be coupled to the implantable medical device via at least one lead port in the header portion.

The electrode arrangement may, for example, be formed by a single electrode element. In another embodiment, the electrode arrangement may be formed by an arrangement of multiple electrode elements.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily under-stood with reference to the following detailed description and the embodiments shown in the drawings. Herein.

DETAILED DESCRIPTION

Figure 1:
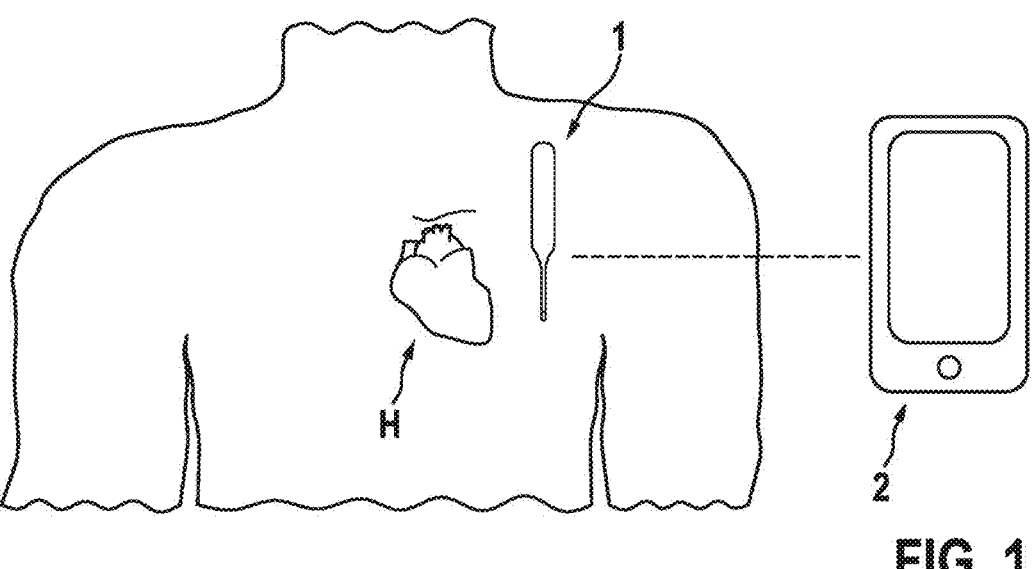
FIG. 1 shows a schematic drawing of an implantable medical device implanted in a patient.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

Referring to FIG. 1, in one embodiment an implantable medical device 1 is implanted (for example, subcutaneously) into a patient for serving a therapeutic and/or diagnostic function.

The implantable medical device 1 may, for example, be a sensor device for measuring biological signals and may be implanted subcutaneously within a patient in proximity to the patient's heart H, for example left-pectorally, in order to sense biological signals from the patient's heart H, such as electrocardiogram (ECG) signals. In another embodiment, the implantable medical device 1 may be a stimulation device, such as a cardiac stimulation device, for example a pacemaker device or a cardioverter defibrillator. In yet another embodiment, the implantable medical device 1 may be a recording device, such as a loop recorder or the like.

In an implanted state, the implantable medical device 1, e.g., shall sense signals and shall transfer information relating to sensed signals to an external communication device 2, for example within a home monitoring system. For this, the implantable medical device 1 may employ a standardized communication technology, such as the Zigbee technology or the Bluetooth Low Energy (BLE) technology.

Figure 2:
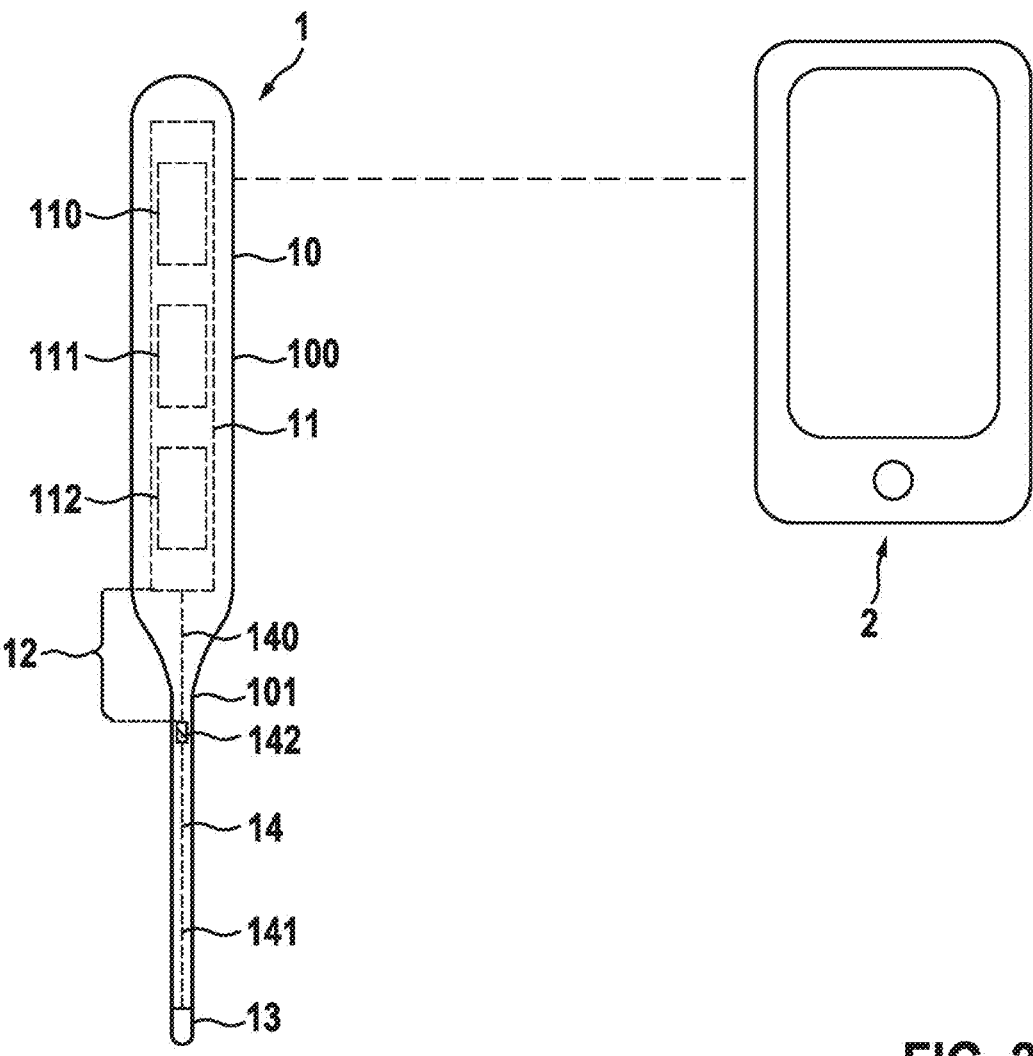
FIG. 2 shows a schematic view of an embodiment of an implantable medical device together with an external communication device.
Figure 3:
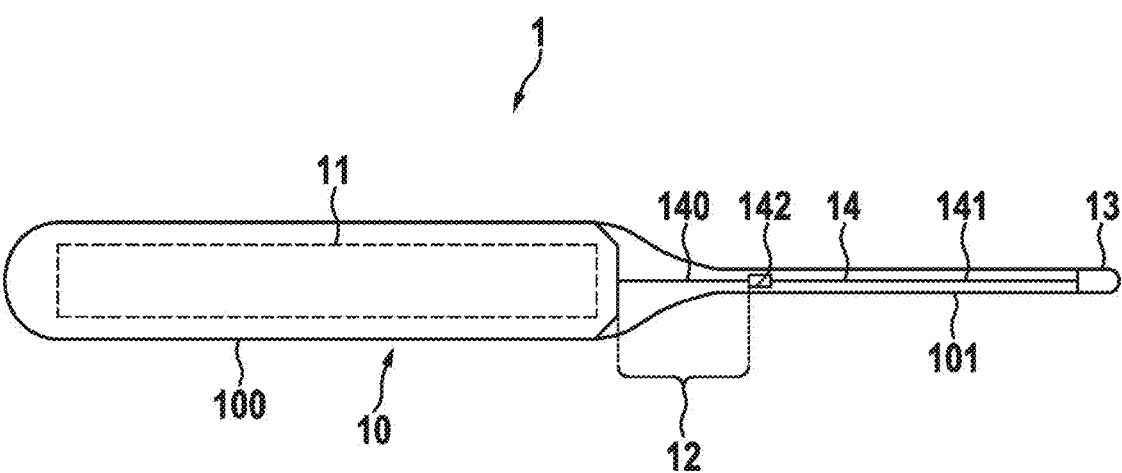
FIG. 3 shows a schematic view of an implantable medical device comprising an electrical line for connecting an electrode arrangement to an electronics module, the electrical line forming an antenna for establishing a communication to an external communication device.

Referring now to FIGS. 2 and 3, in one embodiment the implantable medical device 1 is a loop recorder comprising a housing 10 forming a main housing portion 100 and a header portion 101 linearly extending from the main housing portion 100. An electronics module 11 is arranged within the main housing portion 100, the electronics module 11 forming a communication circuitry 110 for establishing a communication with an external communication device 2. Further, the electronics module 11 comprises a processing circuitry 112 for processing signals for stimulation or sensing, and an energy storage 111 for supplying energy in the shape of a battery for operating the implantable medical device 1.

The header portion 101 comprises an electrode arrangement 13, for example in the shape of a single electrode element, which is arranged at a distal end of the header portion 101 and hence at a remote location with respect to the electronics module 11 arranged within the main housing portion 100.

The electrode arrangement 13 is connected to the electronics module 11 by means of an electrical line 14 extending linearly along the header portion 101. The electrical line 14 serves to pass signals in between the electronics module 11 and the electrode arrangement 13 in order to provide sensed signals from the electrode arrangement 13 to the electronics module 11 and/or to pass stimulation signals for emission to the electrode arrangement 13.

The electrical line 14, in the shown embodiment, in addition serves to form the antenna 12 for establishing a communication to an external communication device 2. Thus, the antenna 12 is an integral and not detachable part of the implantable medical device 1, and/or the antenna 12 is formed by a single wire. In the embodiment of FIG. 3, the electrical line 14 comprises two line sections, a first line section 140 and a second line section 141, which are electrically decoupled from one another at a communication frequency, for example in a communication frequency range corresponding to the Bluetooth Low Energy frequency range, by means of a decoupling element 142.

The decoupling element 142 may, for example, be formed by an inductance having, for example, a value between 5 nH and 50 nH, for example in between 10 nH and 30 nH, for example at 20 nH. The decoupling element 142 at a communication frequency, for example above 1 GHz, comprises a rather large impedance, for example larger than 100 Ohm, preferably larger than 200 Ohm, such that at the communication frequency the line section 140 is electrically decoupled from the line section 141 and the electrode arrangement 13. At physiological frequencies, for example below 10 KHz, the inductance however comprises a small, substantially insignificant impedance, for example below 1 Ohm, preferably below 0.1 Ohm, more preferably smaller than 0.01 Ohm, such that physiological signals may be passed along the electrical line 14 in between the electronics module 11 and the electrode arrangement 13.

In one embodiment, the electrical line 14 is formed by a continuous wire, the line sections 140, 141 hence being formed by the continuous wire. In this embodiment, the decoupling element 142 is, for example, formed by coil windings within the continuous wire.

Herein, the number of required coil windings may be computed, for example, as follows:

Namely, the inductance of a coil in a wire can be calculated by $$L = \mu_0 \frac{N^2 A}{l}$$

where $$\mu_0 = 12.57 \times 10^{-7} \left( \frac{H}{m} \right)$$

N herein is the number of turns, A the cross-sectional area of a turn, and 1 the effective length of the wound section. Assuming the diameter of the turns in the wire to be 1.2 mm, resulting in a cross-sectional area A of $1.13*10^{-6}$ m$^2$, and the net effective length of the decoupling element 142 formed by the turns to be 2.5 mm, six turns are needed to achieve an inductance of ~20 nH in free space.

In another embodiment, the electrical line 14 may be formed by separate wire sections, a first wire section forming the line section 140 and another, separate wire section forming the line section 141. The different wire sections are connected by the decoupling element 142, which in this case, for example, may be formed by a discrete inductor element.

By placing the decoupling element 142 on the electrical line 14 the effective electrical length of line section 140 forming the antenna 12 may be tuned in order to form the antenna 12 for transmission and/or reception of communication signals.

In particular, the decoupling element 142 may be placed on the electrical line 14 such that the line section 140 has a physical length corresponding to an electrical length equal to a quarter wavelength at a communication frequency, for example a center frequency of the Bluetooth Low Energy frequency range.

A quarter wavelength in free space of the Bluetooth Low Energy frequency range (in between 2.4 GHz and 2.4835 GHz) corresponds to a physical length of roughly 31 mm. However, taking into account that the electrical line 14 is encapsulated in a dielectric material, for example a silicone material, in the header portion 101 and further that the implantable medical device 1 in an implanted state is surrounded by tissue, the physical length corresponding to the quarter wavelength is reduced by a factor of about six, such that the antenna 12 should comprise an optimal physical length of about 5 mm.

By suitably placing the decoupling element 142 on the electrical line 14, the physical length of the antenna 12 may be set in order to tune the antenna 12 to an optimal electric length, for example a quarter wavelength.

The decoupling element 142 effectively functions as an RF choke, providing for a decoupling at a communication frequency range, but allowing signals at substantially smaller frequencies, in particular physiological frequencies, to pass.

It should be noted herein that the electrical wavelength of the line section 140 may differ from a quarter wavelength and may, for example, correspond to three quarters of a wavelength or may be electrically even longer. By suitably placing the decoupling element 142 on the electrical line 14 the physical length of the antenna 12 may be set such that an optimum transmission and/or reception may be obtained.

The electrical line 14 extends within the header portion 101. The header portion 101 herein may be flexibly deformable, or may have a rigid shape.

For example, the electrical line 14 is encapsulated by a flexible silicone material. In this case the header portion 11 may, for example, be flexibly bendable.

In another embodiment, the electrical line 14 is encapsulated, for example, in an epoxy, polyurethane or another rigid material, in which case the header portion 101 is substantially rigid.

The electrical line 14 may, for example, be made from an MP35N material, gold, platinum, platinum-iridium, or from a Drawn Filled Tubing (DFT) wire of MP35N with a silver core or with a tantalum core.

If the decoupling element 142 is formed by a discrete inductor, the discrete element may, for example, be connected to the line sections 140, 141 by means of micro-welding, laser welding or another joining technique.

Figure 4:
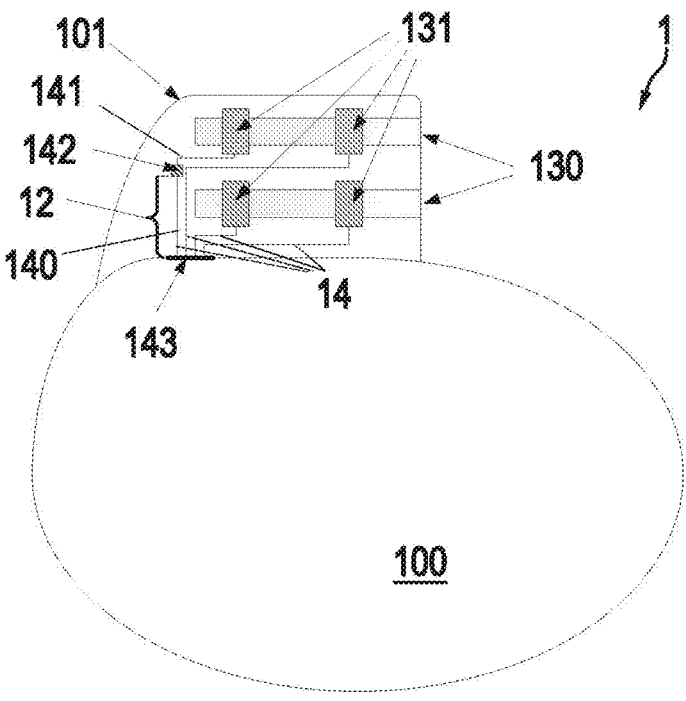
FIG. 4 shows a schematic view of another implantable medical device with ports for lead attachment (lead ports).

Referring now to FIG. 4, in one embodiment the implantable medical device 1 is a pacemaker or implantable cardioverter-defibrillator (ICD). As the loop recorder in FIGS. 2 and 3 this implantable medical device 1 comprises a main housing portion 100, which contains an electronics module (not shown), and a header portion 101 attached to the main housing portion 100.

The header portion 101 comprises lead ports 130 connected to lead connector blocks 131. The lead connector blocks 131 are connected to the electronics module within the main housing portion 100 by means of several electrical lines 14. Each electrical line 14 extends from the electronics module within the main house portion 100 through feedthroughs 143 in the wall of the main house portion 100 into the header portion 101.

One of the electrical lines 14 is divided into two line sections 140, 141 by a decoupling element 142, a first line section 140 between one of the feedthroughs 143 and the decoupling element 142, and a second line section 141 between the decoupling element 142 and one of the lead connector blocks 131. The first line section 140 is electrically decoupled from the second line section at a 141 at a specified communication frequency, e.g., a communication frequency corresponding to a Bluetooth Low Energy frequency. Thus, the first line section 140 forms an antenna 12.

Of course, more than only one electrical line 14 may be divided into two line sections 140, 141 in order to perform the described functions. All of the functions of the device 1 described in FIGS. 2 and 3 are also possible for this device 1 in FIG. 4.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable medical device
10 Housing
100 Main housing portion
101 Header portion
11 Electronics module
110 Communication circuitry
111 Energy storage
112 Processing circuitry
12 Antenna
13 Electrode arrangement
130 Lead ports
131 Lead connector blocks
14 Electrical line (wire)
140, 141 Line section
142 Decoupling element (choke)
143 Feedthroughs
2 External communication device
H Heart

The invention claimed is:

1. An implantable medical device, comprising:
an electronics module comprising communication circuitry for at least one of transmitting communication signals to and receiving communication signals from an external communication device, and further comprising processing circuitry for at least one of processing sensed biological signals and generating stimulation signals for emission;
an electrode arrangement for at least one of sensing said biological signals of a patient and emitting said stimulation signals;
an antenna for at least one of transmitting and receiving said communication signals; and
an electrical line extending in between the electronics module and the electrode arrangement, wherein the electrical line comprises a first line section, a second line section and a decoupling element, the first line section being electrically decoupled from the second line section by the decoupling element and forming said antenna.

2. The implantable medical device according to claim 1, wherein said communications signals are RF signals.

3. The implantable medical device according to claim 1, wherein said communication signals are in a communication frequency range above 500 MHz.

4. The implantable medical device according to claim 1, wherein the first line section is formed to have length equal to a quarter wavelength at a communication frequency.

5. The implantable medical device according to claim 1, wherein the first line section comprises a length in between 2 mm and 20 mm.

6. The implantable medical device according to claim 1, wherein the decoupling element is configured to block signals in said communication frequency range and to pass signals in a physiological frequency range below said communication frequency range.

7. The implantable medical device according to claim 1, wherein the decoupling element comprises an inductance.

8. The implantable medical device according to claim 7, wherein the inductance comprises an inductance value in between 5 nH and 50 nH.

9. The implantable medical device according to claim 1, wherein the electrical line is formed by a continuous wire, the decoupling element being formed by at least one coil winding arranged in between the first line section and the second line section.

10. The implantable medical device according to claim 1, wherein the electrical line is formed by discontinuous wire sections, a first wire section forming said first line section and a second wire section forming said second line section.

11. The implantable medical device according to claim 10, wherein the decoupling element is formed by a discrete inductor arranged in between the first line section and the second line section.

12. The implantable medical device according to claim 1, wherein the electrical line is encapsulated by an electrically insulating housing.

13. The implantable medical device according to claim 1, wherein the electrical line is formed from an MP35N wire, a gold wire, a platinum wire, a platinum-iridium wire, a Drawn Filled Tubing wire of MP35N with a silver core, or a Drawn Filled Tubing wire of MP35N with a tantalum core.

14. The implantable medical device according to claim 1 comprising a housing forming a main housing portion and a header portion extending from the main housing portion, the electronics module being arranged in or on the main housing portion and the electrical line being arranged in or on the header portion.

15. The implantable medical device according to claim 14, wherein the electrical line extends longitudinally along the header portion, the electrode arrangement being arranged on an end of the header portion distal with respect to the main housing portion.

* * * * *